(12) United States Patent
Tsuruno et al.

(10) Patent No.: US 11,378,574 B2
(45) Date of Patent: Jul. 5, 2022

(54) REAGENT FOR DETECTING TARGET SUBSTANCE CONTAINING SUGAR CHAIN, DETECTION METHOD, CARRIER USED IN DETECTION OF TARGET SUBSTANCE CONTAINING SUGAR CHAIN, AND METHOD FOR MANUFACTURING SAID CARRIER

(71) Applicant: SYSMEX CORPORATION, Kobe (JP)

(72) Inventors: Chikayuki Tsuruno, Kobe (JP); Shinya Nagai, Kobe (JP); Minako Terao, Kobe (JP); Chika Mizuta, Kobe (JP); Takuya Kyoutou, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 1453 days.

(21) Appl. No.: 15/245,426

(22) Filed: Aug. 24, 2016

(65) Prior Publication Data

US 2016/0363586 A1    Dec. 15, 2016

Related U.S. Application Data (63) Continuation of application No. PCT/JP2015/052700, filed on Jan. 30, 2015.

(30) Foreign Application Priority Data

Feb. 27, 2014   (JP) .............................. JP2014-036777
Jan. 9, 2015    (JP) .............................. JP2015-002865

(51) Int. Cl.
*G01N 33/53*    (2006.01)
*G01N 33/574*   (2006.01)

(52) U.S. Cl.
CPC ... *G01N 33/5308* (2013.01); *G01N 33/57484* (2013.01); *G01N 2333/4724* (2013.01); *G01N 2400/00* (2013.01)

(58) Field of Classification Search
None
See application file for complete search history.

(56) References Cited

U.S. PATENT DOCUMENTS

| | | | |
|---|---|---|---|
| 6,232,130 B1 * | 5/2001 | Wolf ................. | A61B 5/14532 435/14 |
| 8,623,608 B2 | 1/2014 | Narimatsu et al. | |
| 2007/0202535 A1 | 8/2007 | Hirabayashi et al. | |
| 2012/0172247 A1 | 7/2012 | Narimatsu et al. | |
| 2014/0057286 A1 | 2/2014 | Narimatsu et al. | |
| 2015/0329602 A1 | 11/2015 | Sato et al. | |
| 2018/0106814 A1 | 4/2018 | Narimatsu et al. | |

FOREIGN PATENT DOCUMENTS

| | | |
|---|---|---|
| CN | 102356316 A | 2/2012 |
| CN | 103403011 A | 11/2013 |
| EP | 2405269 A1 | 1/2012 |
| EP | 2 455 758 A1 | 5/2012 |
| JP | 2008-032520 A | 2/2008 |
| JP | 2012-185172 A | 9/2012 |
| KR | 10-2012-0047938 A | 5/2012 |
| WO | 2005/064333 A1 | 7/2005 |
| WO | 2010100862 A1 | 9/2010 |
| WO | 2011/007797 A1 | 1/2011 |
| WO | 2012/108424 A1 | 8/2012 |
| WO | 2012104051 A1 | 8/2012 |
| WO | 2014/098112 | 6/2014 |

OTHER PUBLICATIONS

G. Deknudt, "Cell Kinetics and Radiosensitivity of Human Lymphocytes Stimulated by Phytohemagglutinin, Wistaria Floribunda or Lentil Lectin", Canadian Journal of Genetics and Cytology, vol. 24, No. 6, XP 009194824, pp. 761-769.
G. Cheung et al., "Purification and Properties of the Hemagglutinin from Wistaria floribunda Seeds", Biochemistry, 1979, vol. 18. No. 9, XP 55387703, pp. 1646-1650.
Takashi Sato et al., "Engineering of recombinant Wisteria floribunda agglutinin specifically binding to GalNAcβ1,4GlcNAc (LacdiNAc)", Glycobiology, 2017, XP 55387697, pp. 1-12.
International Search Report of PCT/JP2015/052700 dated Apr. 21, 2015, (2 pages).
Kurokawa, T., et al., "Purification and Characterization of a Lectin from Wistaria floribunda Seeds", The Journal of Biological Chemistry, vol. 251, No. 18, Issue of Sep. 25, 1976, pp. 5686-5693 (9 pages).
Decision of Refusal dated Feb. 9, 2021 in a counterpart Japanese patent application No. 2019-113736.
P. M. Kaladas et al: "Purification and Properties of a Mitogenic Lectin from Wistaria floribunda Seeds", Biochemistry, vol. 18, No. 22, 1979, pp. 4806-4812.
Toshiaki Osawa et al: "Cross-Linked Derivatives of Concanavalin A", Methods in Enzymology, 1987, vol. 150, pp. 17-28.
Satoshi Toyoshima et al: "Lectins from Wistaria floribunda Seeds and Their Effect on Membrane Fluidity of Human Peripheral Lymphocytes", The Journal of Biological Chemistry, 1975, vol. 250, No. 5, pp. 1655-1660.
Japanese Office Action dated Jul. 7, 2020 in a counterpart Japanese patent application No. 2019-113736.
Japanese Office Action dated Jul. 6, 2021 in a counterpart Japanese patent application No. 2019-113736.
Indian Examination Report dated Nov. 28, 2019 in a counterpart Indian patent application No. 201637031879.
Hearing Notice issued on Nov. 25, 2020 in a counterpart Indian patent application No. 201637031879.

* cited by examiner

*Primary Examiner* — Ellen J Marcsisin
(74) *Attorney, Agent, or Firm* — Sughrue Mion, PLLC (57) ABSTRACT

The present invention relates to a method for detecting a target substance that is useful for detection of a glycoprotein and the like comprising a specific sugar chain, a reagent for detecting a target substance, a carrier and a method for manufacturing the carrier.

6 Claims, 8 Drawing Sheets

REAGENT FOR DETECTING TARGET SUBSTANCE CONTAINING SUGAR CHAIN, DETECTION METHOD, CARRIER USED IN DETECTION OF TARGET SUBSTANCE CONTAINING SUGAR CHAIN, AND METHOD FOR MANUFACTURING SAID CARRIER

CROSS-REFERENCE TO RELATED APPLICATION

This application is a continuation of international application PCT/JP2015/052700 filed on Jan. 30, 2015, which claims benefit of Japanese patent applications JP2014-036777 and JP 2015-002865 filed on Feb. 27, 2014 and Jan. 9, 2015, respectively. The entirety of the scope of claims, description, drawings and abstract of these priority applications are incorporated herein by reference.

BACKGROUND OF THE INVENTION

The present invention relates to a reagent for detecting a target substance. More specifically, the present invention relates to a method for detecting a target substance that is useful for detection of a glycoprotein and the like comprising a specific sugar chain, a reagent for detecting a target substance, a carrier and a method for manufacturing the carrier.

Generally, a sugar chain is a compound composed of a plurality of monosaccharides that are covalently bonded via a glycoside bond. Such a sugar chain binds, for example, with a protein or a lipid to form a glycoprotein or a glycolipid.

As a method for analyzing a target substance comprising a sugar chain or the like, for example, a method of analyzing such a sugar chain or a target substance by using lectin that binds to the sugar chain is proposed (see US 2007/202535 and US 2012/172247, for example).

The method disclosed in US 2007/202535 is a method of analyzing the structure of a sugar chain by utilizing the interaction between a protein showing interaction with the sugar chain, and the sugar chain or the sugar chain on a glycoconjugate. The method disclosed in US 2007/202535 uses an array in which lectin, which is a protein showing interaction with the sugar chain, is immobilized on a plate via a compound having an epoxy group as an active group.

The method disclosed in US 2012/172247 is a method of measuring Mac-2 binding protein (hereinafter, also referred to as "M2BP") by using lectin of *Wisteria floribunda* (*Wisteria floribunda* Agglutinin) (hereinafter, also referred to as "WFA") which is lectin that binds with a sugar chain of M2BP which is a glycoprotein. The method disclosed in US 2012/172247 uses, as the lectin, for example, magnetic particles to which biotinylated lectin in which biotin is bound to the lectin, is immobilized via streptavidin, or an array to which the lectin is immobilized.

In these methods disclosed in US 2007/202535 and US 2012/172247, the lectin is immobilized on a solid phase in the condition that a subunit structure of natural lectin is retained so as to present the activity of lectin sufficiently for detecting a sugar chain.

SUMMARY OF THE INVENTION

Although lectin is required to keep a steric structure during the reaction with a sugar chain, it is difficult to keep the steric structure of lectin for a long time in a solution and thus it is difficult to ensure the sufficient reactivity.

The present invention was devised in light of the circumstances of the conventional art. An object of the present invention is to provide a reagent for detecting a target substance having high reactivity on the target substance and having high storage stability, a carrier to be used for detecting a target substance, and a method for manufacturing the carrier and a method for detecting a target substance capable of ensuring high sensitivity and high reproducibility.

One aspect of the present invention includes a reagent for detecting a target substance comprising a sugar chain that binds with WFA, wherein the reagent comprises a dimeric WFA immobilized carrier comprising a solid phase carrier and a dimeric WFA, and the dimeric WFA is immobilized on the solid phase carrier.

Since the reagent for detecting a target substance of the present embodiment comprises a dimeric WFA immobilized carrier, it keeps bindability with a sugar chain, particularly, a sugar chain having a N-acetyl-D-galactosamine [IUPAC name: 2-(acetylamino)-2-deoxy-D-galactose] residue (hereinafter, also referred to as "GalNAc residue") at its terminal, and also it has higher reactivity with the sugar chain in comparison with a reagent comprising a carrier in which naturally occurring WFA (tetrameric WFA) is immobilized on a solid phase carrier, and has excellent storage stability. Therefore, by using the reagent for detecting a target substance of the present embodiment for detection of a target substance comprising a sugar chain, it is possible to ensure high sensitivity and high reproducibility.

In the reagent for detecting a target substance of the present embodiment, it is preferred that the dimeric WFA is immobilized on the solid phase carrier via biotin and biotin-binding protein.

In the reagent for detecting a target substance of the present embodiment, it is preferred that the dimeric WFA is biotinylated dimeric WFA, and the biotin-binding protein is immobilized on the solid phase carrier, and the biotinylated dimeric WFA is immobilized on the solid phase carrier via the biotin-binding protein.

Further aspect of the present invention includes a method for detecting a target substance comprising a sugar chain that binds with WFA, comprising the steps of: (A) bringing a dimeric WFA immobilized carrier comprising a solid phase carrier and a dimeric WFA which is immobilized on the solid phase carrier, a sample comprising the target substance, and a labeling substance that specifically binds with the target substance into contact with each other to form a complex comprising the dimeric WFA, the target substance and the labeling substance on the solid phase carrier, and (B) measuring the labeling substance in the complex obtained in the step (A) to detect the target substance.

The method for detecting a target substance of the present embodiment employs the operation of bringing a dimeric WFA immobilized carrier, and a sample comprising a target substance into contact with each other to form a complex comprising the dimeric WFA and the target substance on the solid phase carrier. Since such an operation is employed, according to the method for detecting a target substance of the present embodiment, it is possible to allow the dimeric WFA and a sugar chain of the target substance to bind with each other with high reactivity and excellent efficiency. Therefore, according to the method for detecting a target substance of the present embodiment, it is possible to ensure high sensitivity. Also, the dimeric WFA used in the dimeric WFA immobilized carrier has excellent storage stability.

Therefore, according to the method for detecting a target substance of the present embodiment, it is possible to ensure high reproducibility.

In the method for detecting a target substance of the present embodiment, it is preferred that the labeling substance is a labeled antibody that specifically binds with the target substance.

A still further aspect of the present invention includes a carrier to be used for detecting a target substance comprising a sugar chain that binds with WFA, wherein the carrier has dimeric WFA formed by dimerization of WFA and a solid phase carrier, and the dimeric WFA is immobilized on the solid phase carrier.

In the carrier of the present embodiment, the dimeric WFA is immobilized on the solid phase carrier. Therefore, the carrier of the present embodiment has higher reactivity with the sugar chain in comparison with the carrier in which naturally occurring WFA (tetrameric WFA) is immobilized on the solid phase carrier, and has excellent storage stability. By using the WFA immobilized reagent of the present embodiment for detecting a target substance comprising a sugar chain, it is thus possible to ensure high sensitivity and high reproducibility.

A further aspect of the present invention includes a method for manufacturing a carrier to be used for detecting a target substance comprising a sugar chain that binds with WFA, comprising the steps of: (I) dimerizing WFA to obtain dimeric WFA, and (II) immobilizing the dimeric WFA obtained in the step (I) on a solid phase carrier to obtain a dimeric WFA immobilized carrier.

The method for manufacturing a carrier of the present embodiment employs the operation of dimerizing WFA, and immobilizing the obtained dimeric WFA on a solid phase carrier. Since such an operation is employed, according to the method for manufacturing a carrier of the present embodiment, it is possible to obtain a WFA immobilized carrier having higher reactivity with the sugar chain in comparison with a carrier on which naturally occurring WFA (tetrameric WFA) is immobilized, and having excellent storage stability.

In the method for manufacturing a carrier of the present embodiment, it is preferred to prepare biotinylated dimeric WFA by mixing a solution comprising a cross-linking agent comprising biotin, and WFA in the step (I).

Also, in the method for manufacturing a carrier of the present embodiment, it is preferred to use a carrier on which biotin-binding protein is immobilized as the solid phase carrier in the step (II), and to immobilize dimeric WFA on the solid phase carrier by letting the biotin-binding protein in the carrier and biotinylated dimeric WFA bind with each other.

In the method for manufacturing a carrier of the present embodiment, it is preferred to obtain the dimeric WFA by bringing a solution comprising a cross-linking agent into contact with WFA so that the molar ratio of WFA to the cross-linking agent is less than or equal to 1/10 (excluding 0) in the step (I).

Further, in the method for manufacturing a carrier of the present embodiment, it is preferred that the cross-linking agent is a cross-linking agent that forms a bridge together with an amino group in dimeric WFA. Such a cross-linking agent preferably has at least one functional group selected from the group consisting of a N-hydroxysuccinimide ester group, an isothiocyano group, a chlorosulfone group, a chlorocarbonyl group, an oxyethylene group, a chloroalkyl group having 1 to 4 carbon atoms, an aldehyde group and a carboxyl group as a reactive group with an amino group in dimeric WFA.

It is also preferred that biotin and the reactive group bind to each other via a spacer.

According to the present invention, it is possible to provide a reagent for detecting a target substance having high reactivity with a target substance and excellent storage stability, a carrier to be used for detecting a target substance, a method for manufacturing the carrier, and a method for detecting a target substance capable of ensuring high sensitivity and high reproducibility.

DETAILED DESCRIPTION OF THE EMBODIMENTS (Reagent for Detecting Target Substance)

A reagent for detecting a target substance of the present embodiment (hereinafter, also referred to as "reagent of the present embodiment") is a reagent for detecting a target substance comprising a sugar chain that binds with lectin of *Wisteria floribunda* (WFA), and characterized in that the reagent comprises a dimeric WFA immobilized carrier in which dimeric WFA formed by dimerization of WFA is immobilized on a solid phase carrier.

Naturally occurring lectin of *Wisteria floribunda* is a tetrameric protein composed of four subunits. In the present description, the tetrameric *Wisteria floribunda* lectin is written simply as "WFA" or written as "tetrameric WFA" unless otherwise specified. In the present description, the product obtained by altering tetrameric WFA into dimer is written as "dimeric WFA". A dimeric WFA is composed of two subunits.

WFA (tetrameric WFA) binds with a sugar chain having a GalNAc residue at its terminal (see Piller et al., Eur. J. Biochem., 191, 461-466 (1990)). WFA (tetrameric WFA) also binds with a sugar chain having a galactose (Gal) residue at its terminal. In the present embodiment, it is preferred that a sugar chain having a GalNAc residue is a target substance. The present inventors found that dimeric WFA that is obtained by altering tetrameric WFA into dimer also has an activity of binding with the sugar chain as described above. The present inventors also found that the reagent involving a solid phase carrier on which the dimeric WFA is immobilized shows higher reactivity than the reagent involving a solid phase carrier on which tetrameric WFA is immobilized. Further, the present inventors found that the storage stability of the present reagent is significantly higher than the storage stability of the reagent involving tetrameric WFA. The present invention is based on these findings.

As described above, since the reagent of the present embodiment comprises a dimeric WFA immobilized carrier on which dimeric WFA is immobilized, it has high reactivity with the sugar chain, and has excellent storage stability. By using the reagent for detecting a target substance of the present embodiment for detecting a target substance comprising a sugar chain, it is thus possible to ensure high sensitivity and high reproducibility.

In the present description, a target substance comprising a sugar chain that binds with the WFA is a substance comprising a sugar chain having a GalNAc residue or a Gal residue at its terminal. Non-limiting examples of the target substance comprising a sugar chain that binds with the WFA include glycoproteins and glycolipids such as M2BP, α1 acidic glycoprotein (AGP), Muc-1, neural cell adhesion molecule L1 (L1CAM), and KL-6 antigen. These target substances are common in comprising a sugar chain having a GalNAc residue or a Gal residue at its terminal and binding with WFA.

M2BP and AGP are used as markers for fibrosis of liver and liver cancer. Therefore, the detection result of M2BP and AGP by the reagent of the present embodiment can be an index for determining the fibrosis level of the liver of the subject.

Muc-1 is used as a marker of bile duct cancer. Therefore, the detection result of Muc-1 by the reagent of the present embodiment can be an index for presence or absence of bile duct cancer in the bile duct of the subject.

L1CAM is used as a tumor marker for bile duct cancer, colon cancer, breast cancer, tumors of nervous system or mesothelium and the like. Therefore, the detection result of L1CAM by the reagent of the present embodiment can be an index for presence or absence of a tumor in the bile duct, colon, breast, nervous system, mesothelium and the like of the subject.

KL-6 antigen is known as a marker for interstitial pneumonia. Therefore, the detection result of KL-6 antigen by the reagent of the present embodiment can be an index for determining the fibrosis level of the lung of the subject.

The solid phase carrier used in the reagent of the present embodiment may be, for example, particles, a plate, or a membrane. Examples of particles to be used include magnetic particles, polystyrene particles, and latex particles. Examples of a plate to be used include a glass plate, a silicone plate, and a plate made of polystyrene. Examples of a membrane to be used include a nitrocellulose membrane, and a poly(vinylidene fluoride) membrane. When particles are used as the solid phase carrier, it is preferred that the particles are dispersed in a solvent. Examples of a solvent include purified water, and a buffer solution. Among the above-described solid phase carriers, it is preferred to use magnetic particles because of easiness of separation between the solid phase carrier and the reaction solution, and replacement with the solvent.

When the magnetic particles are used as the solid phase carrier, it is desired that the mean particle diameter of the magnetic particles is appropriately determined depending on the intended use or the like of the dimeric WFA immobilized carrier because it differs depending on the intended use or the like of the dimeric WFA immobilized carrier of the present embodiment. The mean particle diameter of the magnetic particles is typically 1 to 3 µm, preferably 1.5 to 2.5 µm, more preferably 1.8 to 2.2 µm. The aforementioned mean particle diameter is a value determined by measurement according to the light scattering method using a laser diffraction particle size distribution measuring device (Shimadzu Corporation, product name: SALD series).

Preferably, the dimeric WFA is immobilized on the solid phase carrier via biotin and biotin-binding protein. The biotin-binding protein is not particularly limited as long as it has the bindability with biotin, and examples include avidin, streptavidin, and Tamavidin (registered trade name).

When biotin and biotin-binding protein are used, preferably, the dimeric WFA is biotinylated dimeric WFA, and the biotin-binding protein is immobilized on the solid phase carrier, and the biotinylated dimeric WFA is immobilized on the solid phase carrier via the biotin-binding protein. In this case, the amount of biotin-binding protein immobilized on the solid phase carrier varies depending on the intended use or the like of the dimeric WFA immobilized carrier, and thus it can be appropriately determined depending on the intended use or the like of the dimeric WFA immobilized carrier.

A content of the dimeric WFA immobilized carrier in the reagent of the present embodiment varies depending on the intended use or the like of the reagent of the present embodiment, and thus desirably, it is determined appropriately depending on the intended use of the reagent of the present embodiment. A content of the dimeric WFA immobilized carrier in the reagent of the present embodiment is preferably greater than or equal to 0.1% by mass, more preferably greater than or equal to 0.48% by mass from the view point of the binding capacity, and is preferably less than or equal to 2% by mass, more preferably less than or equal to 1% by mass from the view point of stirring efficiency in an automated analyzer.

The reagent of the present embodiment may comprise a labeling substance. The labeling substance includes a signal generating substance and a target substance binding part. The signal generating substance binds with the target substance via the target substance binding part.

The signal generating substance may be a substance that generates a signal, or may have a substance that brings about generation of a signal. More specifically, examples of the substance that generates a signal include fluorescent dyes and radioactive isotopes. The substance that brings about generation of a signal may be a substance that brings about generation of a signal such as luminescence, fluorescence or color development in a reaction solution by catalyzing the chemical reaction. More specifically, examples of the substance that brings about generation of a signal include enzymes such as alkaline phosphatase and peroxidase. When the enzyme is used, a substrate is reacted with the enzyme, and luminescence, fluorescence or color development from the reaction product is detected.

The target substance binding part is not particularly limited as long as it specifically binds with a target substance. As the target substance binding part, preferably, an antibody specifically binding with a target substance is used. The target substance binding part may be composed of a primary substance (e.g., antibody) that specifically binds with a target substance, and a substance (e.g., labeled antibody) that binds with the primary substance and contains a signal generating substance. In this case, the signal generating substance binds with a target substance via two kinds of antibodies. Although the signal generating substance may be bound to a target substance via three or more kinds of antibodies, it is necessary to take the possibility into account that the number of reaction steps increases and the detection sensitivity deteriorates. The antibody used as the target substance binding part can be easily prepared by immunizing an animal by using the whole or part of the target substance comprising a sugar chain, and a binding site between the target substance and WFA by a common method as described, for example, in Current Protocols in Immunology (John E. Coligan ed., John Wiely & Sons, Inc, 1992). Labeling of the antibody by a labeling substance can be easily conducted by a method suited for the kind of the labeling substance. In the present embodiment, in place of using the antibody, an antibody fragment obtained by a treatment with peptidase or the like after purification of the antibody may be used.

The labeling substance is preferably a labeled antibody that specifically binds with the target substance.

The reagent of the present embodiment may appropriately comprise a stabilizer, a pH modifier, a chelating agent, a non-specific reaction inhibitor, an antiseptic and the like.

The dimeric WFA immobilized carrier and the labeling substance can be provided as a reagent kit in which they are each contained in separate containers. In the present description, a "reagent" includes a reagent kit. The reagent kit may also comprise a washing solution contained in a separate container. When the labeling substance has an enzyme, a substrate for the enzyme may further be contained.

As described in the above, since the reagent of the present embodiment has high reactivity with a sugar chain having a GalNAc residue or a Gal residue at its terminal, and is excellent in storage stability, high sensitivity and high reproducibility can be ensured when the reagent is used for detecting a substance comprising a sugar chain having a GalNAc residue or a Gal residue at its terminal. Therefore, the reagent of the present embodiment is useful for detection (qualitative detection or quantitative detection) of a target substance comprising a sugar chain, particularly a target substance comprising a sugar chain having a GalNAc residue or a Gal residue at its terminal.

(Dimeric WFA Immobilized Carrier and Method for Manufacturing Thereof)

The dimeric WFA immobilized carrier of the present embodiment is a carrier to be used for detecting a target substance comprising a sugar chain that binds with WFA, and characterized in that the carrier has dimeric WFA and a solid phase carrier, wherein the dimeric WFA is immobilized on the solid phase carrier.

Thus, the dimeric WFA immobilized carrier of the present embodiment has high reactivity with a sugar chain having a GalNAc residue or a Gal residue at its terminal, and is excellent in storage stability because the dimeric WFA is immobilized on the solid phase carrier. By using the dimeric WFA immobilized reagent of the present embodiment for detection of a target substance comprising the sugar chain, it is possible to ensure high sensitivity and high reproducibility.

The dimeric WFA solid phase carrier of the present embodiment is the same as the dimeric WFA immobilized carrier contained in the above-described reagent of the present embodiment.

Next, a method for producing the carrier (multimeric WFA solid phase carrier) of the present embodiment (hereinafter, also referred to as "the manufacturing method of the present embodiment") will be described. The manufacturing method of the present embodiment is a method for manufacturing a dimeric WFA immobilized carrier to be used for detecting a target substance comprising a sugar chain that binds with WFA, and characterized in that the method comprises the steps of:

(I) dimerizing the WFA to obtain dimeric WFA, and (II) immobilizing the dimeric WFA obtained in the step (I) on a solid phase carrier to obtain the dimeric WFA immobilized carrier.

In the manufacturing method of the present embodiment, first, WFA is altered into dimer to obtain dimeric WFA (step (I)). The step (I) is conducted by a method of altering tetrameric WFA into dimer. In general, dissociation of subunits of protein is often conducted with a sulfhydryl reagent (SH reagent) that reacts with a sulfhydryl group in the protein. In the present embodiment, however, it is possible to alter tetrameric WFA into dimer efficiently by bringing a cross-linking agent comprising biotin into contact with tetrameric WFA.

In the step (I), when a cross-linking agent comprising biotin is used, the cross-linking agent is preferably a cross-linking agent that forms a bridge with an amino group in the tetrameric WFA. More specifically, examples of the cross-linking agent include cross-linking agents having at least one functional group selected from the group consisting of a N-hydroxysuccinimide ester group, an isothiocyano group, a chlorosulfone group, a chlorocarbonyl group, an oxyethylene group, a chloroalkyl group having 1 to 4 carbon atoms, an aldehyde group and a carboxyl group as a reactive group with an amino group in the tetrameric WFA. By using the aforementioned cross-linking agent, it is possible to alter tetrameric WFA into dimer efficiently.

From the view point of improving reactivity with WFA, handleability in manufacturing and reactivity at the time of detection of a target substance, it is preferable that the cross-linking agent comprising biotin has a structure that biotin and the reactive group are bound via a spacer. Non-limiting examples of the spacer include an aminohexanoyl group (i.e., aminocaproyl group).

In the case where the cross-linking agent is used in the step (I), it is possible to obtain dimeric WFA by bringing a solution comprising a cross-linking agent into contact with the WFA. More specifically, in the case where the cross-linking agent comprising biotin is used in the step (I), dimeric WFA comprising biotin (e.g., biotinylated dimeric WFA) can be prepared by mixing a solution comprising the cross-linking agent comprising biotin and WFA. A molar ratio of WFA/cross-linking agent is preferably less than or equal to 1/10, more preferably less than or equal to 1/20. On the other hand, the lower limit of the molar ratio of WFA/cross-linking agent can be determined appropriately depending on the intended use or the like of the WFA immobilized carrier within the range that the dimeric WFA can be obtained. The molar ratio of WFA/cross-linking agent can be greater than or equal to 1/100 in consideration of the balance between the use amount of the cross-linking agent and the yield of generated dimeric WFA.

Next, the dimeric WFA obtained in the step (I) is immobilized on a solid phase carrier to obtain a dimeric WFA immobilized carrier (step (II)). Immobilization of the dimeric WFA onto a solid phase carrier is not particularly limited, and for example, specific binding between biotin and biotin-binding protein, electrostatic interaction, hydrophobic interaction, hydrogen bond, covalent bond, physical adsorption by denaturation action and the like can be utilized.

In the case where dimeric WFA comprising biotin is prepared by mixing a solution comprising a cross-linking agent comprising biotin and WFA in step (I), it is preferred to immobilize the dimeric WFA on the solid phase carrier by using a carrier on which biotin-binding protein is immobilized as the solid phase carrier, and binding the biotin-binding protein in the carrier with the biotinylated dimeric WFA in step (II).

As described above, the dimeric WFA immobilized carrier of the present embodiment shows higher reactivity with a sugar chain having a GalNAc residue or a Gal residue at its terminal, in comparison with a carrier on which naturally occurring WFA is immobilized, and has excellent storage stability. By using it for detection of a substance comprising a sugar chain having a GalNAc residue or a Gal residue at its terminal, high sensitivity and high reproducibility can be ensured. Therefore, the dimeric WFA immobilized carrier of the present embodiment is useful for detection (qualitative detection or quantitative detection) of a target substance comprising a sugar chain, in particular, a target substance comprising a sugar chain having a GalNAc residue or a Gal residue at its terminal.

(Method for Detecting Target Substance)

The detection method of the present embodiment is a method for detecting a target substance comprising a sugar chain that binds with WFA (hereinafter, also referred to as "the detection method of the present embodiment").

In the detection method of the present embodiment, first, a dimeric WFA immobilized carrier, a sample comprising the target substance and a labeling substance are brought into contact with each other to form a complex comprising the dimeric WFA, the target substance and the labeling substance on the solid phase carrier (step (A)).

In the step (A), the dimeric WFA immobilized carrier of the afore-described embodiment can be used as the dimeric WFA immobilized carrier.

In the step (A), as the labeling substance, a labeling substance contained in the afore-described reagent of the present embodiment can be used.

In the step (A), the order in which the dimeric WFA immobilized carrier, the sample comprising a target substance, and the labeling substance are brought into contact with each other is not particularly limited. In other words, the contacting order may be any of the following (a) to (c):

(a) first, the dimeric WFA immobilized carrier and the sample are brought into contact with each other, and then the labeling substance is brought into contact with the obtained mixture;

(b) first, the dimeric WFA immobilized carrier and the labeling substance are brought into contact with each other, and then the sample is brought into contact with the obtained mixture; and (c) first, the sample and the labeling substance are brought into contact with each other, and then the dimeric WFA immobilized carrier is brought into contact with the obtained mixture.

In the step (A), since the amount of the dimeric WFA immobilized carrier that is brought into contact with the sample varies depending on the kind of the sample, the amount of dimeric WFA in the dimeric WFA immobilized carrier, the storage condition of the dimeric WFA immobilized carrier (liquid storage, freeze-dried storage) and the like, it is desirably determined appropriately depending on the kind of the sample, the amount of dimeric WFA in the dimeric WFA immobilized carrier, the storage condition of the dimeric WFA immobilized carrier (liquid storage, freeze-dried storage) and the like.

The temperature at the time of bringing the sample and the dimeric WFA immobilized carrier into contact with each other may be a temperature at which the steric structure of dimeric WFA is maintained, and is suited for conducting the binding reaction between dimeric WFA and a sugar chain. The temperature is typically 4 to 50° C., preferably 15 to 42° C.

After bringing the sample and the dimeric WFA immobilized carrier into contact with each other, it is preferred to wash the obtained product to remove the free target substance and the free dimeric WFA immobilized carrier that do not form the complex. Examples of the washing agent used for washing the product include, but not limited to a washing agent comprising a buffer, a surfactant, bovine serum albumin (BSA) and the like; purified water and the like.

Next, a target substance in the complex obtained in the step (A) is detected (step (B)).

In the step (B), a target substance in a complex can be detected by measuring a signal generated from the labeling substance in the complex. When the labeling substance contains a fluorescent dye or a radioisotope, a signal such as fluorescence or radioactivity can be measured. When the labeling substance is an enzyme, by letting a substrate of the enzyme react with the complex, a signal such as luminescence, fluorescence or color development generated from the product of the enzyme reaction can be measured. Since the measurement result correlates with the amount of the target substance, the target substance can be detected qualitatively or quantitatively.

EXAMPLES

Hereinafter, the present invention will be specifically described by way of examples and so on, however, the present invention is not limited to these. In the following, the mean particle diameter is a value obtained by measurement according to the light scattering method using a laser diffraction particle size distribution measuring device (Shimadzu Corporation, product name: SALD series).

Experimental Example 1

WFA (VECTOR Laboratories, product name: *Wisteria floribunda* Lectin) was added to a 20 mM phosphate buffer (pH 7.5) so that the concentration of the WFA was 2.5 mg/mL to prepare a solution comprising WFA.

To the obtained solution comprising WFA, 5-(N-succinimidyloxycarbonyl)pentyl D-biotin amide (DOJINDO LABORATORIES, product name: Biotin-AC5-Osu) which is a cross-linking agent comprising biotin was added so that WFA/cross-linking agent (molar ratio) was 1/100. By incubating the obtained solution at 25° C. for 90 minutes, the WFA and the cross-linking agent comprising biotin were caused to react with each other to obtain a reaction product.

Experimental Examples 2 to 5

A reaction product was obtained by conducting the same operation as in Experimental example 1 except that the WFA/cross-linking agent (molar ratio) was 5/100 (Experimental example 2), 10/100 (Experimental example 3), 25/100 (Experimental example 4) or 50/100 (Experimental example 5) in place of employing the WFA/cross-linking agent (molar ratio) of 1/100 in Experimental example 1.

Test Example 1

Figure 1:
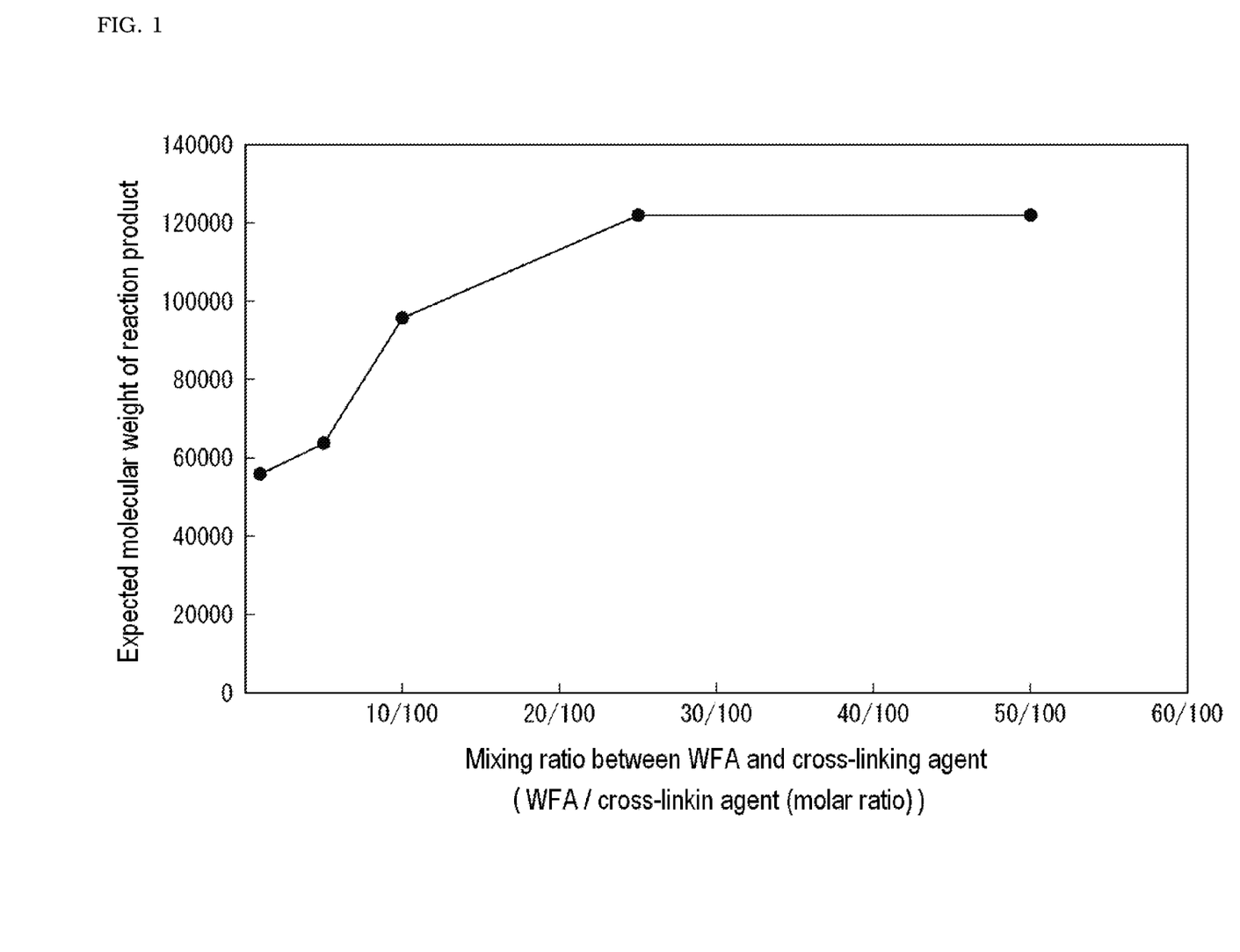
FIG. 1 is a graph showing the examination result of the relationship between the mixing ratio between the WFA and the cross-linking agent, and the expected molecular weight of the reaction product in Test Example 1.

Each of the reaction products obtained in Experimental examples 1 to 5 was analyzed in the following conditions by a high performance liquid chromatography to determine an expected molecular weight of the reaction product.
Elution solvent: phosphate buffer solution (pH 6.5)
Separation column: gel filtration column
(TOSOH CORPORATION, product name: TSK gel G3000SWXL)
Molecular weight marker:
Thyroglobulin (molecular weight 669000)
γ-globulin (molecular weight 158000)
Ovalbumin (molecular weight 44000)
Myoglobin (molecular weight 17000)
Vitamin 12 (molecular weight 13000)
FIG. 1 shows the examination result of the relationship between the mixing ratio between the WFA and the cross-linking agent, and the expected molecular weight of the reaction product in Test Example 1. The theoretical value of the molecular weight of the biotinylated tetramer WFA (hereinafter, also referred to as "biotinylated tetrameric WFA") is 116000. The theoretical value of the molecular weight of the biotinylated dimer WFA (hereinafter, also referred to as "biotinylated dimeric WFA") is 58000. The theoretical value of the molecular weight of the biotinylated monomer WFA (hereinafter, also referred to as "biotinylated monomeric WFA") is 29000.

As shown in FIG. 1, when the mixing ratio (volume ratio) between the WFA and the cross-linking agent is greater than or equal to 25/100 (Experimental examples 4 and 5), the expected molecular weight of the reaction product is 122000. This suggests that the reaction products obtained in Experimental examples 4 and 5 are biotinylated tetrameric WFA.

When the mixing ratio between the WFA and the cross-linking agent is less than 25/100 (Experimental examples 1 to 3), it is demonstrated that the expected molecular weight of the reaction product tends to decrease as the mixing ratio decreases. Since the expected molecular weight of the reaction product is 56000 when the mixing ratio between the WFA and the cross-linking agent is 1/100 (Experimental example 1), it is suggested that the reaction product obtained in Experimental example 1 is biotinylated dimeric WFA. Since the expected molecular weight of the reaction product is 64000 when the mixing ratio is 5/100 (Experimental example 2), it is suggested that in most cases, the reaction product obtained in Experimental example 2 is dimerized WFA. Further, since the expected molecular weight of the reaction product is 96000 when the mixing ratio is 10/100 (Experimental example 3), it is suggested that the reaction product obtained in Experimental example 3 is a mixture of biotinylated dimeric WFA and biotinylated tetrameric WFA.

Therefore, these results suggest that biotinylated dimeric WFA can be obtained when the mixing ratio (volume ratio) between the WFA and the cross-linking agent is less than or equal to 10/100.

Example 1

(1) Preparation of Solution Comprising WFA

WFA (VECTOR Laboratories, product name: *Wisteria floribunda* Lectin) was added to a 20 mM phosphate buffer (pH 7.5) so that the concentration of the WFA was 2.5 mg/mL to prepare a solution comprising WFA.

(2) Reaction of WFA and Cross-Linking Agent

To the solution comprising WFA obtained in Example 1 (1), 5-(N-succinimidyloxycarbonyl)pentyl D-biotin amide (DOJINDO LABORATORIES, product name: Biotin-AC5-Osu) which is a cross-linking agent in which biotin and a reactive group are bound via a spacer was added as a cross-linking agent comprising biotin so that the WFA/cross-linking agent (molar ratio) was 1/100. By incubating the obtained solution at 25° C. for 90 minutes, the WFA and the cross-linking agent were reacted with each other, and a reaction product was obtained.

(3) Purification of Biotinylated Dimeric WFA

The reaction product obtained in Example 1 (2) was purified in the following conditions by a high performance liquid chromatography to obtain biotinylated dimeric WFA.
Elution solvent: phosphate buffer solution (pH 6.5)
Separation column: gel filtration column
(TOSOH CORPORATION, product name: TSK gel G3000SWXL)

(4) Preparation of Solution Comprising STA-Bound Particles

A complex in which streptavidin is immobilized on the surface of magnetic particles (the mean particle diameter 2 μm) (the amount of streptavidin per 1 g of magnetic particles: 2.9 to 3.5 mg; hereinafter also referred to as "STA-bound magnetic particles") was washed three times with a 0.01 M HEPES buffer (pH 7.5). The STA-bound magnetic particles after washing were added to a 0.01 M HEPES buffer (pH 7.5) so that the STA concentration was 18 to 22 μg/mL (the concentration of STA-bound magnetic particles was 0.48 to 0.52 mg/mL) to obtain a solution comprising STA-bound particles.

(5) Preparation of Dimeric WFA Immobilized Carrier

The biotinylated dimeric WFA obtained in Example 1 (3) was added to the solution comprising STA-bound particles obtained in Example 1 (4) so that the concentration of the biotinylated dimeric WFA (dimeric WFA sensitization concentration) was 5 μg/mL (Experiment number 1-1), 10 μg/mL (Experiment number 1-2), 20 μg/mL (Experiment number 1-3) or 30 μg/mL (Experiment number 1-4) to let streptavidin of the STA-bound magnetic particles and biotin of the biotinylated dimeric WFA bind with each other. The obtained product was washed three times with a 0.1 M MES buffer (pH 6.5) to obtain a dimeric WFA immobilized carrier. The obtained dimeric WFA immobilized carrier was suspended in a Good's buffer such as a MES buffer and a HEPES buffer; a phosphate buffer solution or the like, to obtain a solution comprising dimeric WFA immobilized carrier.

Comparative Example 1

(1) Reduction and Biotinylation of WFA

WFA was reduced by mixing 88 μL of a reducing agent (350 mM 2-mercaptoethylamine, NACALAI TESQUE, INC., product name: 2-mercaptoethylamine hydrochloride) and 2000 μg of WFA (VECTOR Laboratories, product name: *Wisteria floribunda* Lectin), and incubating at 25° C. for 90 minutes. Then the obtained reduced WFA was biotinylated with N-biotinyl-N'-[2-(N-maleimide)ethyl]piperazine hydrochloride (DOJINDO LABORATORIES, product name: Biotin-PE-maleimide) to obtain a reaction product.

(2) Calculation of Predicted Molecular Weight

An expected molecular weight of a reaction product was determined by the same operation as in Test Example 1 except that the reaction product obtained in Comparative Example 1 (1) was used in place of the reaction products obtained in Experimental examples 1 to 5 in Test Example 1. As a result, the expected molecular weight of the reaction product obtained in Comparative Example 1 (1) was 29000. This suggests that the reaction product obtained in Comparative Example 1 (1) is biotinylated monomeric WFA.

(3) Purification of Biotinylated Monomeric WFA

Biotinylated monomeric WFA was obtained by conducting the same operation as in Example 1 (3) except that the reaction product obtained in Comparative Example 1 (1) was used in place of the reaction product obtained in Example 1 (2) in Example 1 (3).

(4) Preparation of Monomeric WFA Immobilized Carrier

The biotinylated monomeric WFA obtained in Comparative Example 1 (3) was added to the solution comprising STA-bound particles obtained in Example 1 (4) so that the concentration of the biotinylated monomeric WFA (monomeric WFA sensitization concentration) was 5 μg/mL (Experiment number 2-1), 10 μg/mL (Experiment number 2-2), 20 μg/mL (Experiment number 2-3) or 30 μg/mL (Experiment number 2-4) to let streptavidin of the STA-bound magnetic particles and biotin of the biotinylated monomeric WFA bind to each other. The obtained product was washed three times with a 0.1 M MES buffer (pH 6.5) to obtain a monomeric WFA immobilized carrier. The monomeric WFA immobilized carrier was suspended in a 0.1 M MES buffer (pH 6.5), a 0.1 M HEPES buffer (pH 7.5) or the like to obtain a solution comprising monomeric WFA immobilized carrier.

Comparative Example 2

WFA (VECTOR Laboratories, product name: *Wisteria floribunda* Lectin) was added to the solution comprising STA-bound particles obtained in Example 1 (4) in 5 μg/mL (Experiment number 3-1), 10 μg/mL (Experiment number 3-2), 20 μg/mL (Experiment number 3-3) or 30 μg/mL (Experiment number 3-4) to let streptavidin of the STA-bond magnetic particles and biotin of the biotinylated tetrameric WFA bind with each other. The obtained product was washed three times with a 0.1 M MES buffer (pH 6.5) to obtain a tetrameric WFA immobilized carrier. The tetrameric WFA immobilized carrier was suspended in a 0.1 M MES buffer (pH 6.5), a 0.1 M HEPES buffer (pH 7.5) or the like to obtain a solution comprising tetrameric WFA immobilized carrier.

Test Example 2

50 μL of a 0.01 M HEPES buffer (pH 7.5) and 10 μL of a test sample (0.1 to 100 μg/mL aqueous solution comprising glycoprotein M2BP) were mixed, and incubated at 42° C. for 2 minutes.

To the obtained mixture, 30 μL of the solution comprising dimeric WFA immobilized carrier obtained in Example 1 (Experiment numbers 1-1 to 1-4), the solution comprising monomeric WFA immobilized carrier obtained in Comparative Example 1 (Experiment numbers 2-1 to 2-4) or the solution comprising tetrameric WFA immobilized carrier obtained in Comparative Example 2 (Experiment numbers 3-1 to 3-4) was added. The resultant solution was incubated at 42° C. for 1 minute to let M2BP in the test sample react with the dimeric WFA immobilized carrier, the monomeric WFA immobilized carrier or the tetrameric WFA immobilized carrier.

The obtained reaction product was washed four times with 100 to 700 μL of a washing solution (aqueous solution comprising 20 mM Tris (pH 7.4), 0.1% by mass of Tween 20, 0.1% by mass of sodium azide and 0.8% by mass of sodium chloride).

After washing, 100 μL of a 0.1 U/mL alkaline phosphatase-labeled anti M2BP antibody solution (antibody concentration 0.01 to 100 μg/mL) was added. The obtained mixture was incubated at 42° C. for 2.5 minutes. Then the mixture was washed four times with 100 to 700 μL of the washing solution.

After washing, 50 μL of a reaction solution (an aqueous solution comprising 0.1 M 2-amino-2-methyl-1-propanol (pH 9.6), 1 mM magnesium chloride and 0.1% by mass of sodium azide) and 100 μL of a solution comprising a substrate (APPLIED BIOSYSTEMS, product name: CDP-Star with Sapphirine-II) were added. This was then incubated at 42° C. for 5 minutes to induce the alkaline phosphatase reaction.

Then the luminescence intensity at wavelengths ranging from 300 to 650 nm was measured by using a full-automatic immunoassay device (Sysmex Corporation, product name: HISCL-2000i).

Figure 2:
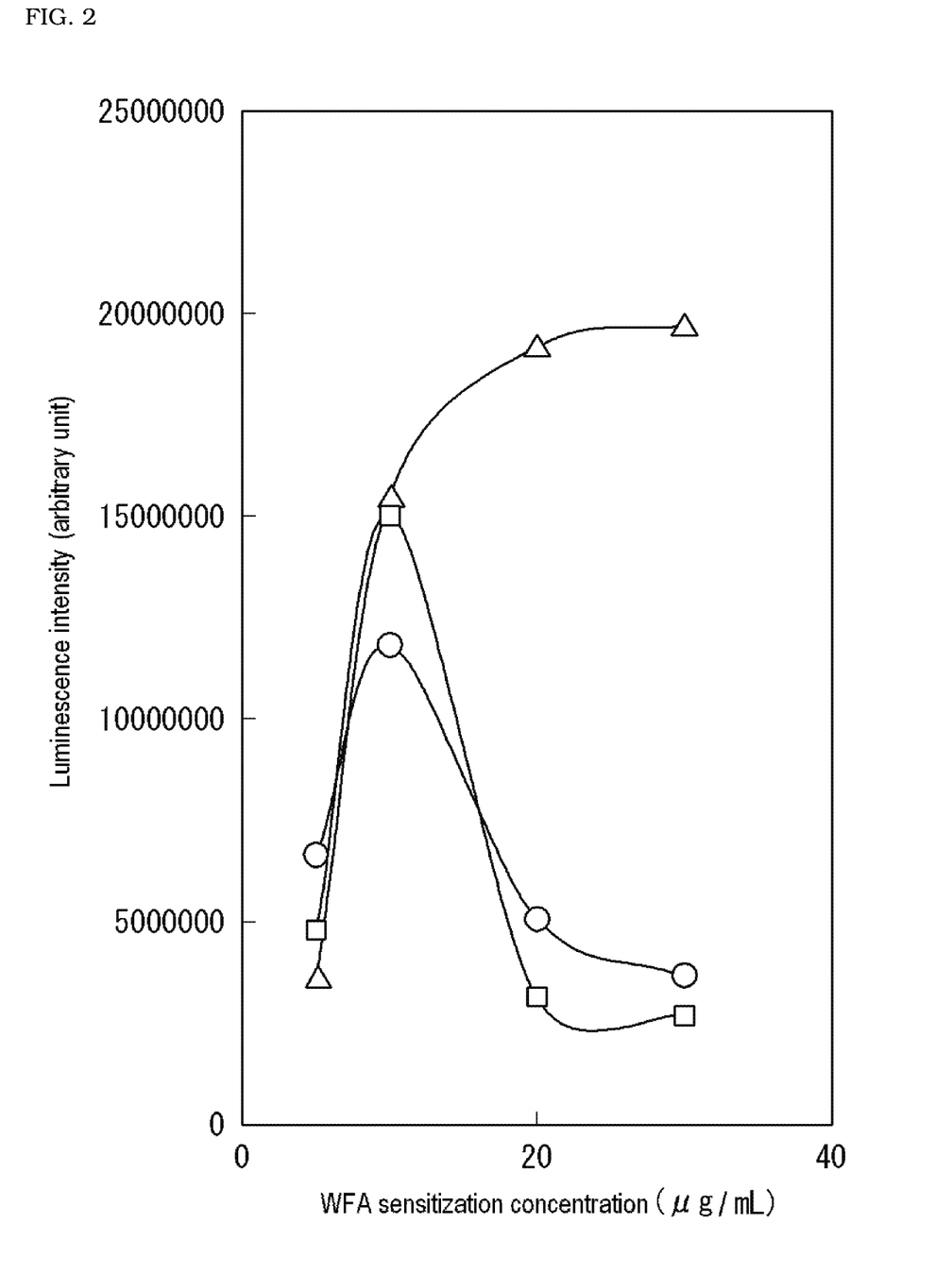
FIG. 2 is a graph showing the examination result of the relationship between the WFA sensitization concentration and the luminescence intensity when M2BP is used as a target substance in Test Example 2.

FIG. 2 shows the examination result of the relationship between the WFA sensitization concentration and the luminescence intensity when M2BP was used as a target substance in Test Example 2. In the chart, the open triangle indicates the luminescence intensity when the solution comprising the dimeric WFA immobilized carrier obtained in Example 1 (Experiment numbers 1-1 to 1-4) was used, the open square indicates the luminescence intensity when the solution comprising the monomeric WFA immobilized carrier obtained in Comparative Example 1 (Experiment numbers 2-1 to 2-4) was used, and the open circle indicates the luminescence intensity when the solution comprising the tetrameric WFA immobilized carrier obtained in Comparative Example 2 (Experiment numbers 3-1 to 3-4) was used.

FIG. 2 reveals that when the dimeric WFA immobilized carrier (open triangle) is used, high luminescence intensity is obtained regardless of the sensitization concentration at a sensitization concentration of greater than or equal to 10 μg/mL. On the other hand, when the monomeric WFA immobilized carrier or the tetrameric WFA immobilized carrier is used, high luminescence intensity is exhibited at a sensitization concentration of greater than or equal to 10 μg/mL, but the luminescence intensity significantly decreases at a sensitization concentration of greater than or equal to 20 μg/mL.

Decrease in the luminescence intensity is attributable to the fact that some obstacle occurs in the steric structure in the binding between M2BP and lectin due to the high sensitization concentration. That is, even if a large quantity of monomeric WFA or tetrameric WFA is used for improving the sensitivity, the sensitivity would decrease conversely. On the other hand, in dimeric WFA, such an obstacle that inhibits the binding with M2BP would not occur even at a high sensitization concentration, revealing that a large quantity of lectin can be sensitized on the solid phase carrier for realizing high sensitivity.

Example 2

A solution comprising dimeric WFA immobilized carrier was obtained by conducting the same operation as in Example 1 except that the WFA/cross-linking agent (molar ratio) was 1/10 (Experiment number 4-1 (WFA sensitization concentration 5 μg/mg, Experiment number 4-2 (WFA sensitization concentration 10 μg/mg, Experiment number 4-3 (20 μg/mL) or Experiment number 4-4 (30 μg/mg) in place of employing the WFA/cross-linking agent (molar ratio) of 1/100 in Example 1.

Example 3

A solution comprising dimeric WFA immobilized carrier was obtained by conducting the same operation as in Example 1 except that the WFA/cross-linking agent (molar ratio) was 1/20 (Experiment number 5-1 (WFA sensitization concentration 5 μg/mg, Experiment number 5-2 (WFA sensitization concentration 10 μg/mg, Experiment number 5-3 (20 μg/mL) or Experiment number 5-4 (30 μg/mL)) in place of employing the WFA/cross-linking agent (molar ratio) of 1/100 in Example 1.

Example 4

A solution comprising dimeric WFA immobilized carrier was obtained by conducting the same operation as in Example 1 except that the WFA/cross-linking agent (molar ratio) was 1/40 (Experiment number 6-1 (WFA sensitization concentration 5 μg/mL), Experiment number 6-2 (WFA sensitization concentration 10 μg/mL), Experiment number 6-3 (20 μg/mL) or Experiment number 6-4 (30 μg/mg) in place of employing the WFA/cross-linking agent (molar ratio) of 1/100 in Example 1.

Example 5

A solution comprising dimeric WFA immobilized carrier was obtained by conducting the same operation as in Example 1 except that the WFA/cross-linking agent (molar ratio) was 1/60 (Experiment number 7-1 (WFA sensitization concentration 5 μg/mL), Experiment number 7-2 (WFA sensitization concentration 10 μg/mL), Experiment number 7-3 (20 μg/mL) or Experiment number 7-4 (30 μg/mL)) in place of employing the WFA/cross-linking agent (molar ratio) of 1/100 in Example 1.

Example 6

A solution comprising dimeric WFA immobilized carrier was obtained by conducting the same operation as in Example 1 except that the WFA/cross-linking agent (molar ratio) was 1/80 (Experiment number 8-1 (WFA sensitization concentration 5 μg/mL), Experiment number 8-2 (WFA sensitization concentration 10 μg/mL), Experiment number 8-3 (20 μg/mL) or Experiment number 8-4 (30 μg/mL)) in place of employing the WFA/cross-linking agent (molar ratio) of 1/100 in Example 1.

Example 7

A solution comprising dimeric WFA immobilized carrier was obtained by conducting the same operation as in Example 1 except that the WFA/cross-linking agent (molar ratio) was 1/120 (Experiment number 9-1 (WFA sensitization concentration 5 μg/mL), Experiment number 9-2 (WFA sensitization concentration 10 μg/mL), Experiment number 9-3 (20 μg/mL) or Experiment number 9-4 (30 μg/mL)) in place of employing the WFA/cross-linking agent (molar ratio) of 1/100 in Example 1.

Example 8

A solution comprising dimeric WFA immobilized carrier was obtained by conducting the same operation as in Example 1 except that the WFA/cross-linking agent (molar ratio) was 1/160 (Experiment number 10-1 (WFA sensitization concentration 5 μg/mL), Experiment number 10-2 (WFA sensitization concentration 10 μg/mL), Experiment number 10-3 (20 μg/mL) or Experiment number 10-4 (30 μg/mL)) in place of employing the WFA/cross-linking agent (molar ratio) of 1/100 in Example 1.

Example 9

A solution comprising dimeric WFA immobilized carrier was obtained by conducting the same operation as in Example 1 except that the WFA/cross-linking agent (molar ratio) was 1/200 (Experiment number 11-1 (WFA sensitization concentration 5 μg/mL), Experiment number 11-2 (WFA sensitization concentration 10 μg/mL), Experiment number 11-3 (20 μg/mL) or Experiment number 11-4 (30 μg/mL)) in place of employing the WFA/cross-linking agent (molar ratio) of 1/100 in Example 1.

Test Example 3

The same operation as in Test Example 2 was conducted except that the solutions comprising dimeric WFA immobilized carriers obtained in Examples 1 to 9 were used in Test Example 2, and the luminescence intensity was measured.

Figure 3:
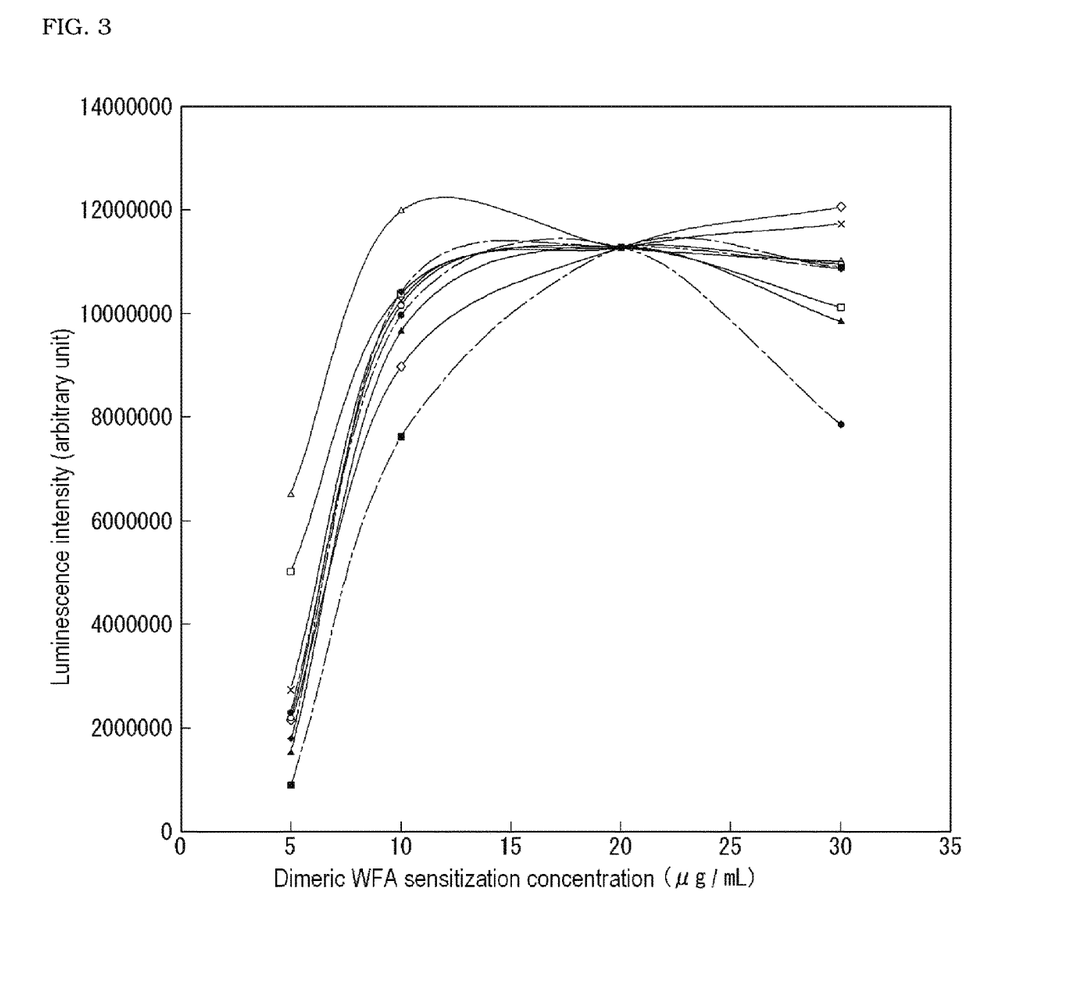
FIG. 3 is a graph showing the examination result of the relationship between the dimeric WFA sensitization concentration and the luminescence intensity when M2BP is used as a target substance in Test Example 3.

FIG. 3 shows the examination result of the relationship between the WFA sensitization concentration and the luminescence intensity when M2BP was used as a target substance in Test Example 3. In the chart, the open rhomboid indicates the luminescence intensity when the solution comprising dimeric WFA immobilized carrier having a WFA/cross-linking agent (molar ratio) of 1/10 was used (Experiment numbers 4-1 to 4-4), the open square indicates the luminescence intensity when the solution comprising dimeric WFA immobilized carrier having a WFA/cross-linking agent (molar ratio) of 1/20 was used (Experiment numbers 5-1 to 5-4), the open triangle indicates the luminescence intensity when the solution comprising dimeric WFA immobilized carrier having a WFA/cross-linking agent (molar ratio) of 1/40 was used (Experiment numbers 6-1 to 6-4), the cross indicates the luminescence intensity when the solution comprising dimeric WFA immobilized carrier having a WFA/cross-linking agent (molar ratio) of 1/60 was used (Experiment numbers 7-1 to 7-4), the open circle indicates the luminescence intensity when the solution comprising dimeric WFA immobilized carrier having a WFA/cross-linking agent (molar ratio) of 1/80 was used (Experiment numbers 8-1 to 8-4), the solid rhomboid indicates the luminescence intensity when the solution comprising dimeric WFA immobilized carrier having a WFA/cross-linking agent (molar ratio) of 1/100 was used (Experiment numbers 1-1 to 1-4), the solid square indicates the luminescence intensity when the solution comprising dimeric WFA immobilized carrier having a WFA/cross-linking agent (molar ratio) of 1/120 was used (Experiment numbers 9-1 to 9-4), the solid triangle indicates the luminescence intensity when the solution comprising dimeric WFA immobilized carrier having a WFA/cross-linking agent (molar ratio) of 1/160 was used (Experiment numbers 10-1 to 10-4), and the solid circle indicates the luminescence intensity when the solution comprising dimeric WFA immobilized carrier having a WFA/cross-linking agent (molar ratio) of 1/200 was used (Experiment numbers 11-1 to 11-4).

FIG. 3 reveals that the luminescence intensity in using the solution comprising dimeric WFA immobilized carrier showed relatively small variation depending on the WFA/cross-linking agent (molar ratio).

Test Example 4

The solution comprising dimeric WFA immobilized carrier obtained in Example 1 (WFA sensitization concentration: 20 µg/mL (Experiment number 1-3)) was incubated at 37° C. for 14 days and sampled over time. Using the sampled solution comprising dimeric WFA immobilized carrier, the same operation as in Test Example 2 was conducted and the luminescence intensity was measured.

Next, a relative value (remaining activity of the dimeric WFA immobilized carrier) of the luminescence intensity when the solution comprising dimeric WFA immobilized carrier after a lapse of a predetermined time was used to the luminescence intensity when the solution comprising dimeric WFA immobilized carrier before incubation was used (control luminescence intensity) was determined. By examining the variation over time of the remaining activity, the storage stability of the dimeric WFA immobilized carrier was evaluated.

Also, the same operation as described above was conducted except that the solution comprising tetrameric WFA immobilized carrier obtained in Comparative Example 2 (WFA sensitization concentration: 10 µg/mL (Experiment number 1-2)) was used in place of the solution comprising dimeric WFA immobilized carrier obtained in Example 1 in the above, and the storage stability of the tetrameric WFA immobilized carrier was evaluated.

Figure 4:
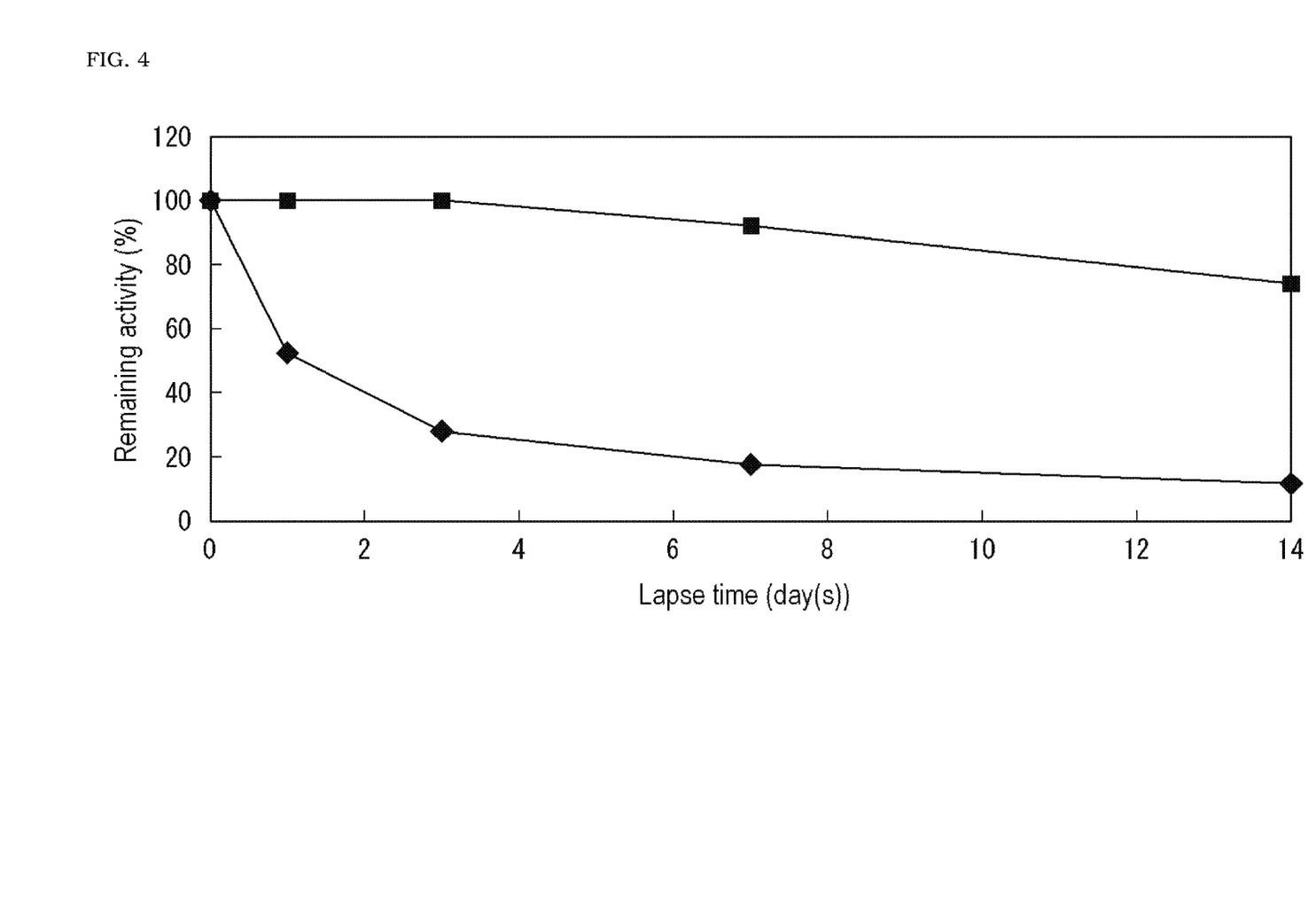
FIG. 4 is a graph showing the examination result of the change over time of the remaining activity when M2BP is used as a target substance in Test Example 4.

FIG. 4 shows the remaining activity when the binding activity with M2BP at the point of day 0 of the lapse time is regarded as 100. In the chart, the solid square indicates the remaining activity of the solution comprising dimeric WFA immobilized carrier, and the solid rhomboid indicates the remaining activity of the solution comprising tetrameric WFA immobilized carrier.

Also as can be seen from FIG. 4, the dimeric WFA immobilized carrier has high remaining activity regarding the binding activity with M2BP after a lapse of 14 days from starting of the incubation. The result shown in FIG. 4 reveals that the remaining activity of the dimeric WFA immobilized carrier is higher than the remaining activity regarding the binding activity of the tetrameric WFA immobilized carrier. This demonstrates that the dimeric WFA immobilized carrier is more excellent in storage stability than the tetrameric WFA immobilized carrier.

Test Example 5

(1) Storage of Dimeric WFA Immobilized Carrier

The solution comprising dimeric WFA immobilized carrier obtained in Example 1 was stored in a refrigerator held at 2 to 8° C. A part of the solution comprising dimeric WFA immobilized carrier was sampled after a lapse of 0 month, after a lapse of 1 month, after a lapse of 3 months, after a lapse of 6 months, after a lapse of 7 months from starting of the storage.

(2) Evaluation of Storage Stability of Dimeric WFA Immobilized Carrier Based on Reactivity with Muc-1

50 µL of a 0.01 M HEPES buffer (pH 7.5) and 10 µL of a serum sample of bile duct cancer patient (PROMMDDX, product name: Bileduct cancer) as a test sample were mixed. The resultant mixture was incubated at 42° C. for 2 minutes.

Then 30 µL of the solution comprising dimeric WFA immobilized carrier sampled in Test Example 5 (1) was added. This was then incubated at 42° C. for 1 minute to let Muc-1 in the test sample and the dimeric WFA immobilized carrier react with each other.

The reaction product was washed four times with 100 to 700 µL of a washing solution (an aqueous solution comprising 20 mM Tris (pH 7.4), 0.1% by mass of Tween 20, 0.1% by mass of sodium azide and 0.8% by mass of sodium chloride).

After washing, 100 µL of a 0.1 U/mL alkaline phosphatase-labeled anti Muc-1 antibody solution was added. The resultant mixture was incubated at 42° C. for 2.5 minutes. Then the mixture was washed four times with 100 to 700 µL of the washing solution.

To the reaction product after washing, 50 µL of a reaction solution (an aqueous solution comprising 0.1 M 2-amino-2-methyl-1-propanol (pH 9.6), 1 mM magnesium chloride and 0.1% by mass of sodium azide) and 100 µL of a solution comprising a substrate (APPLIED BIOSYSTEMS, product name: CDP-Star with Sapphirine-II) were added. This was then incubated at 42° C. for 5 minutes to conduct the alkaline phosphatase reaction.

Then for the obtained reaction product, the luminescence intensity at wavelengths ranging from 300 to 650 nm was measured by using a full-automatic immunoassay device (Sysmex Corporation, product name: HISCL-2000i).

Next, a relative value (remaining activity of the dimeric WFA immobilized carrier) of the luminescence intensity when the solution comprising dimeric WFA immobilized carrier after a lapse of a predetermined time was used to the luminescence intensity when the solution comprising dimeric WFA immobilized carrier before incubation was used (control luminescence intensity) was determined. By examining the variation over time of the remaining activity, the storage stability of the dimeric WFA immobilized carrier was evaluated.

Figure 5:
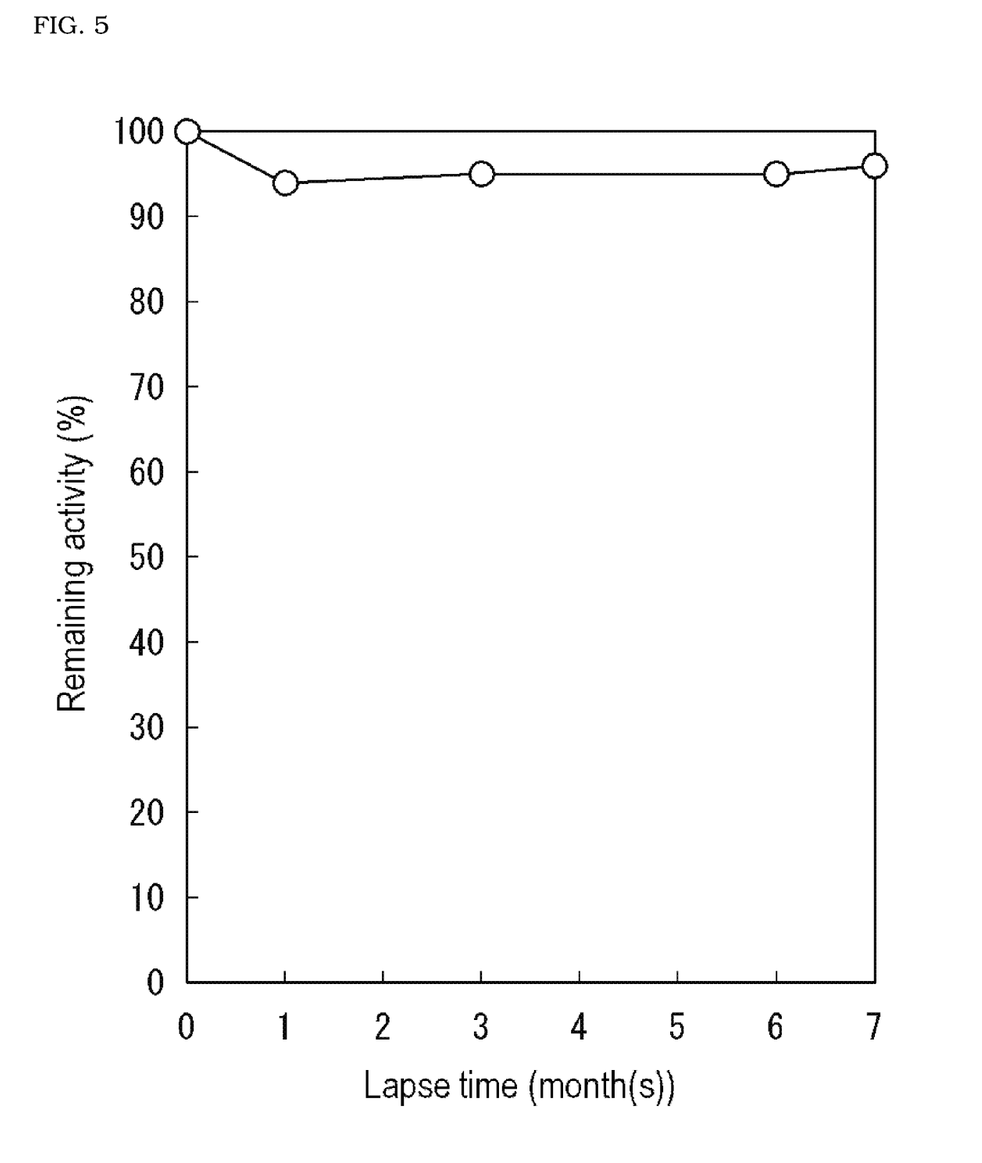
FIG. 5 is a graph showing the examination result of the change over time of the remaining activity when Muc-1 is used as a target substance in Test Example 5.

FIG. 5 shows the remaining activity when the binding activity with Muc-1 at the point of 0 month of the lapse time is regarded as 100.

As shown in FIG. 5, the dimeric WFA immobilized carrier had high remaining activity after a lapse of 7 months from starting of the storage. This reveals that the dimeric WFA immobilized carrier is excellent in storage stability.

Test Example 6

The same operation as in Test Example 5 was conducted except that the solution comprising dimeric WFA immobilized carrier obtained in Example 1 was incubated at 37° C. in place of storing in a refrigerator held at 2 to 8° C., and a part of the solution comprising dimeric WFA immobilized carrier was sampled after a lapse of 0 day, after a lapse of 1 day, after a lapse of 3 days, after a lapse of 7 days, and after a lapse of 14 days from starting of the incubation in place of sampling a part of the solution comprising dimeric WFA immobilized carrier after a lapse of 0 month, after a lapse of 1 month, after a lapse of 3 months, after a lapse of 6 months, and after a lapse of 7 months from starting of the storage, and the storage stability of the dimeric WFA immobilized carrier was evaluated.

Figure 6:
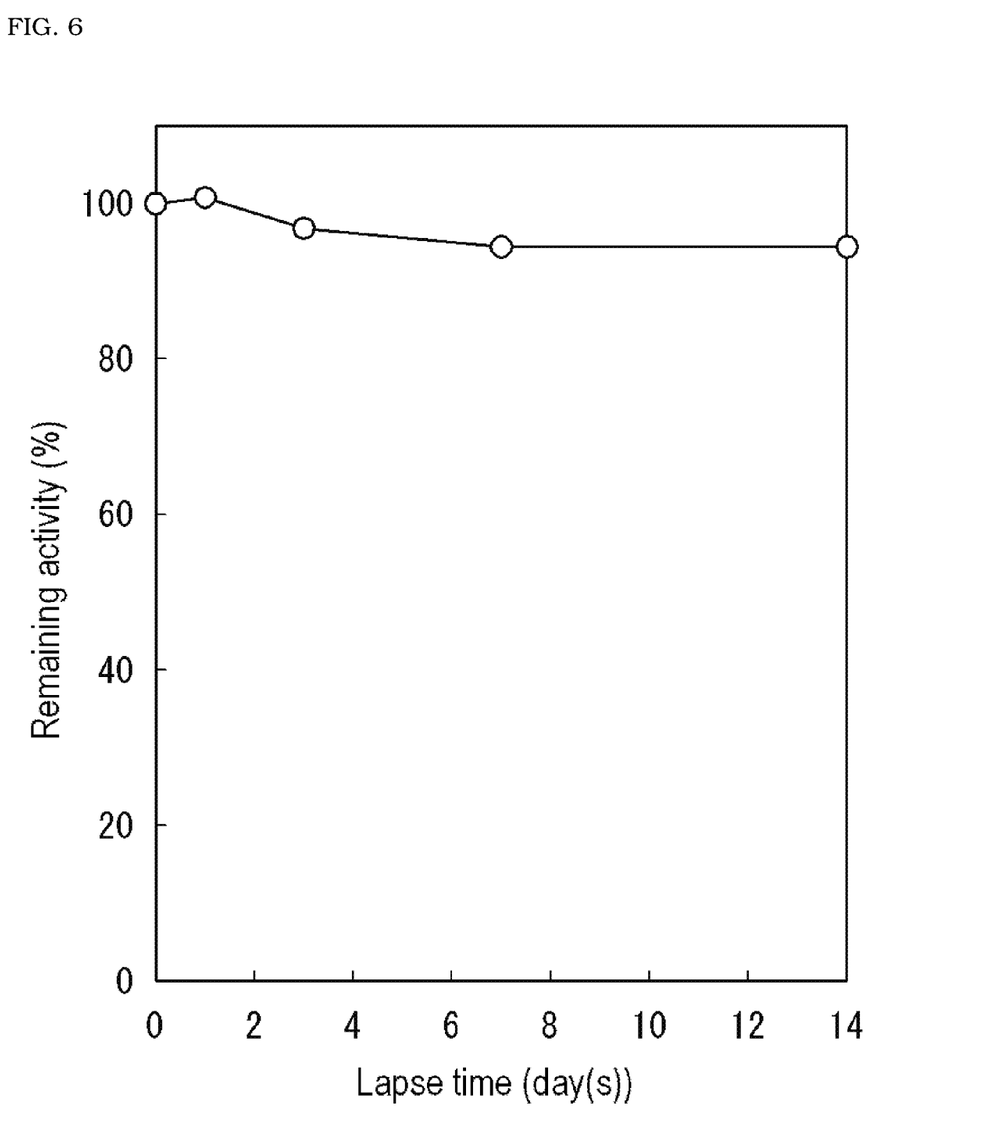
FIG. 6 is a graph showing the examination result of the change over time of the remaining activity when Muc-1 is used as a target substance in Test Example 6.

FIG. 6 shows the remaining activity when the binding activity with Muc-1 at the point of day 0 of the lapse time is regarded as 100.

As shown in FIG. 6, the dimeric WFA immobilized carrier had high remaining activity after a lapse of 14 days from starting of the incubation. This reveals that the dimeric WFA immobilized carrier is excellent in storage stability.

Test Example 7

50 μL of a 0.01 M HEPES buffer (pH 7.5) and 10 μL of a test sample were mixed, and the obtained mixture was incubated at 42° C. for 2 minutes. As the test sample, bile duct cancer patient samples 1 to 3 (supplied from PROM-MDDX, product name: Bileduct cancer) were used.

Then 30 μL of the solution comprising dimeric WFA immobilized carrier obtained in Example 1 (Experiment numbers 1-1 to 1-4), the solution comprising monomeric WFA immobilized carrier obtained in Comparative Example 1 (Experiment numbers 2-1 to 2-4) or the solution comprising tetrameric WFA immobilized carrier obtained in Comparative Example 2 (Experiment numbers 3-1 to 3-4) was added. These were incubated at 42° C. for 1 minute to let Muc-1 in the test sample and the dimeric WFA immobilized carrier react with each other.

The obtained reaction product was washed four times with 100 to 700 μL of a washing solution (an aqueous solution comprising 20 mM Tris (pH 7.4), 0.1% by mass of Tween 20, 0.1% by mass of sodium azide and 0.8% by mass of sodium chloride).

After washing, 100 μL of a 0.1 U/mL alkaline phosphatase-labeled anti Muc-1 antibody solution was added. The resultant mixture was incubated at 42° C. for 2.5 minutes. Then the mixture was washed four times with 100 to 700 μL of the washing solution.

To the reaction product after washing, 50 μL of a reaction solution (an aqueous solution comprising 0.1 M 2-amino-2-methyl-1-propanol (pH 9.6), 1 mM magnesium chloride and 0.1% by mass of sodium azide) and 100 μL of a solution comprising a substrate (APPLIED BIOSYSTEMS, product name: CDP-Star with Sapphirine-II) were added. This was then incubated at 42° C. for 5 minutes to conduct the alkaline phosphatase reaction.

Then the luminescence intensity at wavelengths ranging from 300 to 650 nm was measured by using a full-automatic immunoassay device (Sysmex Corporation, product name: HISCL-2000i). Next, a relative reactivity taking the luminescence intensity when the solution comprising dimeric WFA immobilized carrier in which WFA sensitization concentration was 5 μg/mL (Experiment number 1-1) was used as 100 was determined.

Figure 7A:
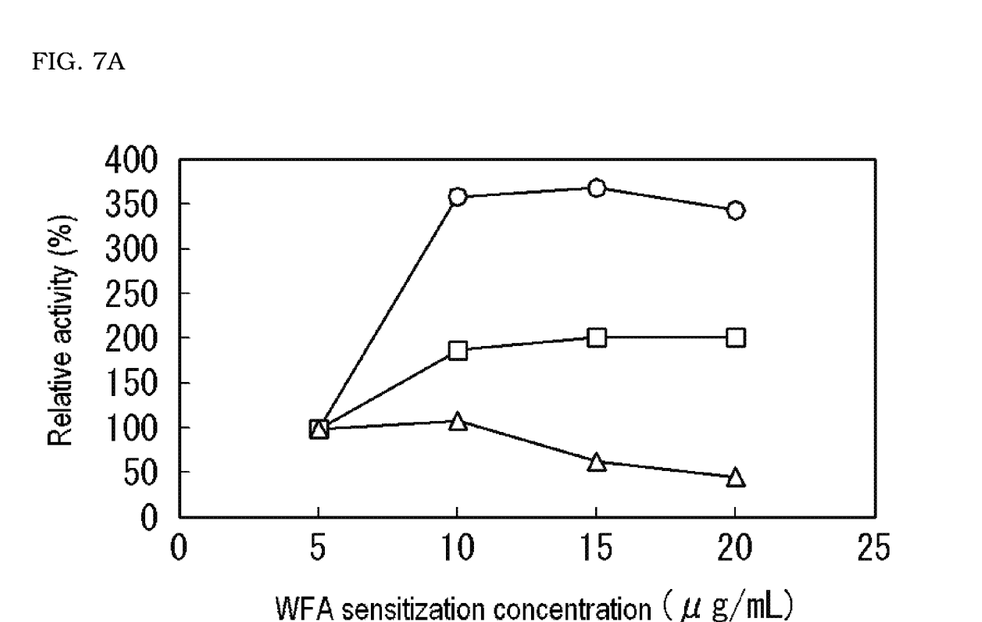
FIG. 7A is a graph showing the examination result of the relationship between the dimeric WFA sensitization concentration and the relative reactivity with Muc-1 using bile duct cancer patient sample 1 in Test Example 7.
Figure 7B:
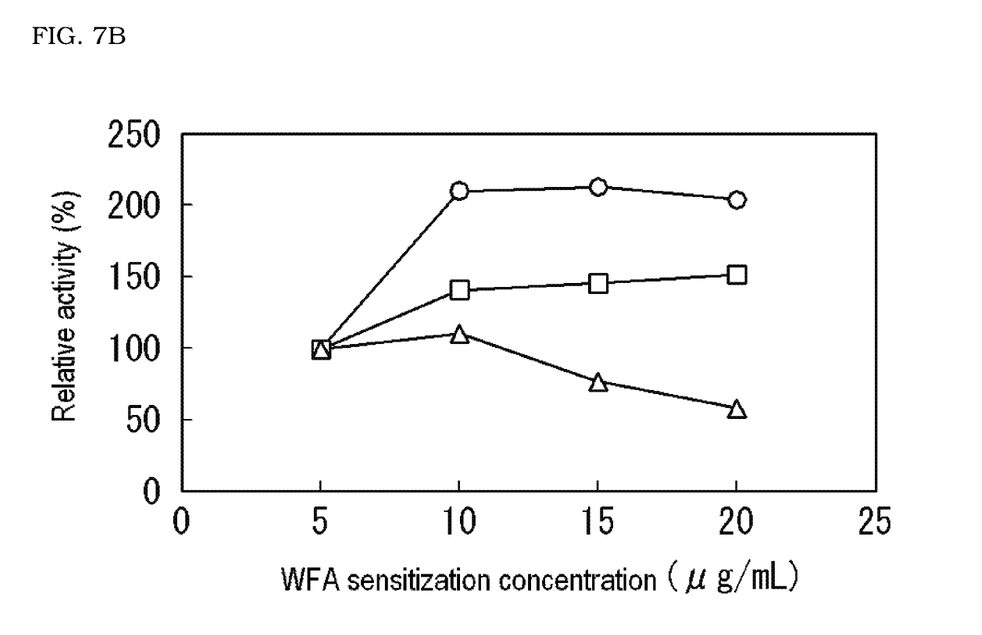
FIG. 7B is a graph showing the examination result of the relationship between the dimeric WFA sensitization concentration and the relative reactivity with Muc-1 using bile duct cancer patient sample 2 in Test Example 7.
Figure 7C:
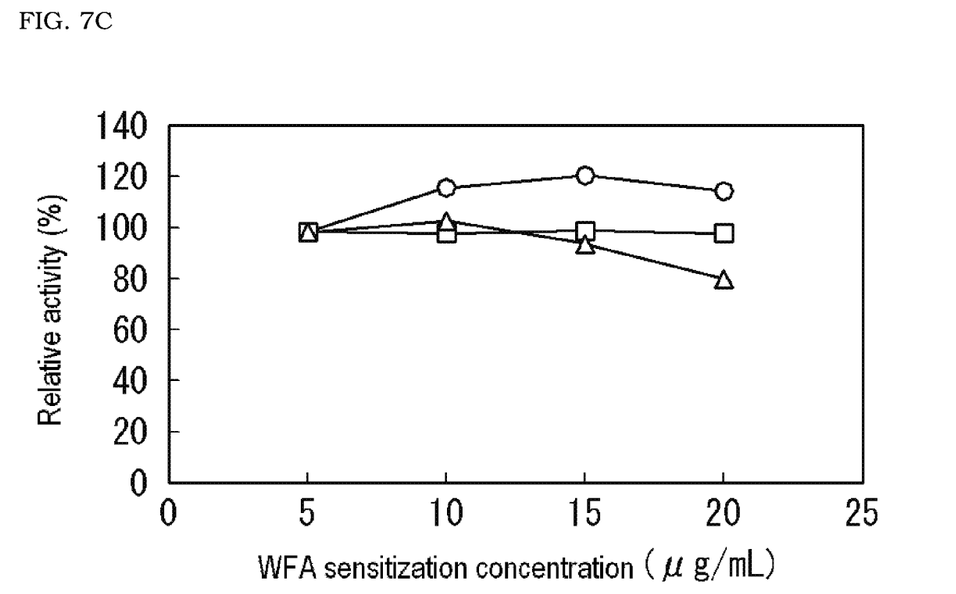
FIG. 7C is a graph showing the examination result of the relationship between the dimeric WFA sensitization concentration and the relative reactivity with Muc-1 using bile duct cancer patient sample 3 in Test Example 7.

FIGS. 7A to C show the examination results of the relationship between the WFA sensitization concentration and the luminescence intensity when Muc-1 was used as a target substance in Test Example 7. In the chart, the open circle indicates the luminescence intensity when the solution comprising dimeric WFA immobilized carrier obtained in Example 1 was used (Experiment numbers 1-1 to 1-4), the open square indicates the luminescence intensity when the solution comprising monomeric WFA immobilized carrier obtained in Comparative Example 1 was used (Experiment numbers 2-1 to 2-4), and the open triangle indicates the luminescence intensity when the solution comprising tetrameric WFA immobilized carrier obtained in Comparative Example 2 was used (Experiment numbers 3-1 to 3-4). FIG. 7A shows the relationship between the dimeric WFA sensitization concentration and the relative reactivity when the bile duct cancer patient sample 1 was used, FIG. 7B shows the relationship between the dimeric WFA sensitization concentration and the relative reactivity when the bile duct cancer patient sample 2 was used, and FIG. 7C shows the relationship between the dimeric WFA sensitization concentration and the relative reactivity when the bile duct cancer patient sample 3 was used.

As shown in FIGS. 7A to C, the relative reactivity in using the dimeric WFA immobilized carrier (open circle) was higher in any case of using the samples 1 to 3 irrespectively of the WFA sensitization concentration, than the relative reactivity in using the monomeric WFA immobilized carrier (open square) or the tetrameric WFA immobilized carrier (open triangle). This reveals that according to the dimeric WFA immobilized carrier, high reactivity is shown with respect to a target substance comprising a sugar chain that binds with WFA such as Muc-1 contained in a sample irrespectively of the WFA sensitization concentration.

These results reveal that the dimeric WFA immobilized carrier has higher reactivity with the sugar chain compared with the tetrameric WFA immobilized carrier and the monomeric WFA immobilized carrier. It is also revealed that the dimeric WFA immobilized carrier is excellent in storage stability.

What is claimed is:

1. A method for detecting a target substance comprising a sugar chain that binds with lectin of *Wisteria floribunda* (WFA), comprising the steps of:
   (A) bringing a dimeric WFA immobilized carrier comprising a solid phase carrier and a dimeric WFA which is immobilized on the solid phase carrier, a sample comprising the target substance, and a labeling substance that specifically binds with the target substance into contact with each other to form a complex comprising the dimeric WFA, the target substance and the labeling substance on the solid phase carrier, and
   (B) measuring the labeling substance in the complex obtained in the step (A) to detect the target substance.

2. The method according to claim 1, wherein the labeling substance is a labeled antibody that specifically binds with the target substance.

3. The method according to claim 1, wherein the dimeric WFA is composed of two subunits.

4. The method according to claim 1, wherein the dimeric WFA is immobilized on the solid phase carrier via biotin and biotin-binding protein.

5. The method according to claim 4, wherein the dimeric WFA is biotinylated dimeric WFA, and the biotin-binding protein is immobilized on the solid phase carrier, and the biotinylated dimeric WFA is immobilized on the solid phase carrier via the biotin-binding protein.

6. The method according to claim 1, wherein the solid phase carrier is a magnetic particle.

* * * * *